United States Patent [19]

Cohen et al.

[11] Patent Number: 5,362,715
[45] Date of Patent: Nov. 8, 1994

[54] MIXTURES OF ACETYLPOLYALKYLINDANES AND ACETYLPOLYALKYLTETRALINES

[75] Inventors: Amnon M. Cohen; Frank E. Conboy, both of Amersfoort; Willem Lenselink, Voorthuizen; Everardus A. Oostveen, Bennekom, all of Netherlands

[73] Assignee: PFW Aroma Chemicals B.V., Nijverheidsweg, Netherlands

[21] Appl. No.: 48,344

[22] Filed: Apr. 15, 1993

[30] Foreign Application Priority Data

Apr. 16, 1992 [EP] European Pat. Off. ........ 92201127.5

[51] Int. Cl.$^5$ ................................................. A61K 7/46
[52] U.S. Cl. .................................... 562/17; 568/323; 585/411
[58] Field of Search .................. 512/17; 568/323; 585/411

[56] References Cited

U.S. PATENT DOCUMENTS

| | | | |
|---|---|---|---|
| 2,997,503 | 8/1961 | Carpenter et al. | 512/17 |
| 3,045,047 | 7/1962 | Davidson et al. | 512/17 |
| 3,509,215 | 4/1970 | Wood et al. | 512/17 |
| 4,551,573 | 11/1985 | Cabb | 585/459 |
| 4,877,912 | 10/1989 | Frank | 585/411 |
| 4,877,915 | 10/1989 | Frank | 585/411 |
| 5,087,770 | 2/1992 | Frank | 512/17 |
| 5,095,152 | 3/1992 | Frank | 512/17 |
| 5,162,588 | 11/1992 | Fehr et al. | 512/17 |

FOREIGN PATENT DOCUMENTS 2910493 10/1979 Germany ................ 512/17

*Primary Examiner*—James H. Reamer
*Attorney, Agent, or Firm*—David Edwards

[57] ABSTRACT

The invention is directed to a mixture of acetylpolyalkylindanes and acetylpolyalkyltetralines obtainable by cycloalkylation of p-cymene and/or p,α-dimethylstyrene and/or 8-p-cymenyl halides and/or 8-p-cymenyl alcohol with a mixture of alkenes consisting of one or more methylbutene isomers and one or more dimethylbutene isomers, followed by acetylation of the intermediate mixture of polyalkylindanes and polyalkyltetralines.

13 Claims, No Drawings

MIXTURES OF ACETYLPOLYALKYLINDANES AND ACETYLPOLYALKYLTETRALINES

BACKGROUND OF THE INVENTION

This invention relates to musk odorants and precursors thereof. More specifically it relates to acetylated mixtures of polyalkylindanes and polyalkyltetralines prepared from a suitable aromatic compound having the p-cymene skeleton and a mixture of alkenes consisting of one or more methylbutene isomers and one or more dimethylbutene isomers.

Through the years considerable effort has been made to arrive at synthetic products exhibiting desirable musk like odors. Typical representatives of such musk odorants belong the class of acetylpolyalkylindanes and acetylpolyalkyltetralines, both with a wide variety of the substitution pattern in the aromatic moiety as well as in the nonaromatic moiety of the molecule. Amongst them are, for example, the commercially successful aroma chemicals Phantolid (R), i.e., 6-acetyl-1,1,2,3,3,5-hexamethylindane and Tonalid (R), i.e., 7-acetyl-1,1,3,4,4,6-hexamethyltetraline, prepared by acetylation of the corresponding hexamethylindane and hexamethyltetraline, respectively, which in turn are prepared by cycloalkylation of usually p-cymene with usually 2-methyl-2-butene and 3,3-dimethylbutene-1, respectively, yielding the said aroma chemicals at purity levels of 95% and above.

Some methods of preparation of polyalkylindanes and polyalkyltetralines are set forth in German patent application 1035826, U.S. Pat. No. 2,759,022, Swiss patent 336377, German patent 1243187, European patent application 89207 and Japanese patent application 8240420 starting from substituted benzenes and aliphatic alkenes, aliphatic alcohols or aliphatic halogenides in the presence of sulphuric acid or Friedel-Crafts catalyst. In U.S. Pat. Nos. 2,851,501, 3,278,621, 3,379,782, 3,379,783, 3,379,784 and 3,379,785, European patent application 61267 and Japanese patent application 7363757 methods of preparation of cycloalkylated aromatic compounds are described starting from substituted isopropenylbenzenes and aliphatic alkenes or aliphatic alcohols in the presence of Lewis acids, proton acids, activated clays or cation exchange resins.

In the U.S. Pat. Nos. 3,246,044, 4,740,646 and Japanese patent application 8275935 the use of substituted or unsubstituted benzyl halides is disclosed as the aromatic reactant in combination with aliphatic alkenes and in the presence of Lewis acid catalysts.

In U.S. Pat. Nos. 4,551,573 and 4,877,912 cycloalkylations catalyzed by aluminum halides and elemental iodine are set forth. In U.S. Pat. No. 3,856,875 a process is claimed for the preparation of 1,1,3,4,4,6-hexamethyl-1,2,3,4-tetrahydronaphtalene which comprises reacting p-cymene with a substantially equimolar solution of 3,3-dimethylbutene-1 and t-alkylhalide in the presence of an effective amount of an aluminum halide catalyst suspended in a reaction compatible solvent. In U.S. Pat. No. 4,284,818 the utilization of alkyl halides is extended to the combination of p-cymene and a 2,3-dimethylbutene in an aliphatic hydrocarbon or cyclohexane solvent. In Japanese patent application 8143221 a similar method of preparation is disclosed for 1,1,3,4,4,6-hexamethyltetraline utilizing a mixture of p-cymene, 3,3-dimethylbutene-1 and an essentially equimolar amount of a primary alkyl chloride, e.g., isobutyl chloride. The combination of alkenes and alkyl halides is also the subject of U.S. Pat. Nos. 4,877,910, 4,877,911, 4,877,914 and 4,877,916. European patent 393742 describes a process starting from a benzyl alcohol and an alkene under the influence of a Lewis acid. In U.S. Pat. Nos. 4,877,910, 4,877,912, 4,877,913, 4,877915 and 4,877,916 the cycloalkylation of substituted benzenes by specific alkenes in the presence of specific olefinic reagents with greater electron releasing properties is set forth.

The acetylation of polyalkylindanes and polyalkyltetralines can be carried out by methods known to the art, e.g., by the interaction with acetic anhydride or an acetyl halide and a suitable catalyst and, for example, according to the methods set forth in European patent applications 89207 and 393742, French patent 8519207 and U.S. Pat. Nos. 3,045,047 and 4,162,256.

SUMMARY OF THE INVENTION

The present invention is directed to a musk odorant composition of a mixture of acetylpolyalkylindanes and acetylpolyalkyltetralines prepared by cycloalkylation of p-cymene and/or p,α-dimethylstyrene and/or 8-p-cymenyl halides and/or 8-p-cymenyl alcohol with a mixture of alkenes of one or more methylbutene isomers and one or more dimethylbutene isomers, followed by acetylation of the intermediate mixture of polyalkylindanes and polyalkyltetralines.

DETAILED DESCRIPTION OF THE INVENTION

In accordance with the invention mixtures thus prepared, surprisingly exhibit more interesting and more useful organoleptic properties than can be expected by one skilled in the art from the single reaction products prepared from p-cymene and/or p,α-dimethylstyrene and/or 8-p-cymenyl halides and/or 8-p-cymenyl alcohol with one or more methylbutene isomers, and prepared from p-cymene and/or p,α-dimethylstyrene and/or 8-p-cymenyl halides and/or 8-p-cymenyl alcohol with one ore more dimethylbutene isomers. Said single reaction products from the methylbutenes or from the dimethylbutenes exhibit a predominantly musk odor, while the odor of the acetylated mixtures according to the invention is far more complete, rounded and perfumistic of character showing novel and highly desirable natural floral and woody notes. The performance of these odor characteristics is especially pronounced on application of the acetylated mixtures of the invention as perfume ingredients for soaps and detergents, resulting in an enhanced odor substantivity after washing and drying of the laundry, which by no means excludes their advantageous application in the other field of perfumery, amongst them alcoholic perfumes, colognes, lotions, cosmetics, functional and technical perfumes and the like.

In accordance with another embodiment of the invention the said novel mixtures of acetylpolyalkylindanes and acetylpolyalkyltetralines shown unexpectedly good solubility characteristics in the usual perfumery solvents, especially in conjunction with the hydrogenated methyl ester of rosin. The most important commercial acetylpolyalkylindanes and acetylpolyalkyltetralines are crystalline solids with relatively high melting points, e.g., 6-acetyl-1,1,2,3,3,5-hexamethylindane at 58° C. minimum and 7-acetyl-1,1,3,4,4,6-hexamethyltetraline at 54° C. minimum. Crystallization and handling of solids in the production process as well as solubilization of the crystalline lumps during the compounding process for perfumes are laborious, time and energy consuming production steps, which also influence the overall organoleptic result negatively.

A liquid or low melting, easy to handle, bulk musk chemical is of a great, commercial importance to the perfume compounding industry. The acetylated indane/tetraline mixtures of the present invention have considerably lower solidification points, depending on the molecular ratio of methylbutene isomers and dimethylbutene isomers reacted, and can easily be compounded with other perfumery ingredients and solvents without the application of heat. A solidification point as low as 32° C. can be obtained with ratios close to 1, also showing the best solubilization properties. For such mixtures of the invention, solutions up to 80% by weight which stay liquid at room temperature can easily be prepared, while for example, 7-acetyl-1,1,3,4,4,6-hexamethyl-tetraline stable solutions at room temperature of at best 50% by weight are hardly attainable. Preferred solvents in this respect are the methylester of rosin, commercially known as e.g., Abalyn ®, and the hydrogenated methylester of rosin, commercially known as, e.g., Hercolyn D ® and Floralyn ®, whether or not mixed with isopropyl myristate.

The invention is also directed to the intermediate mixture obtained from p-cymene and/or p,α-dimethylstyrene and/or 8-p-cymenylhalides and/or 8-hydroxy-p-cymene and a combination of alkenes consisting of one or more methylbutenes selected from the group of 2-methylbutene-2 and 2-methylbutene-1 and one or more dimethylbutenes selected from the group of 3,3-dimethylbutene-1, 2,3-dimethylbutene-1, and 2,3-dimethylbutene-2, which mixture can be acetylated to the required composition.

The invention is illustrated by the following examples, which, however, are not to be interpreted as limiting the invention thereto.

EXAMPLE 1

Cycloalkylation of 629 g of p-cymene with a mixture of 143.5 g of 2-methylbutene-2 and 172.5 g of 2,3-dimethylbutene-1 and 10.8 g of aluminum trichloride at 10° C. according to the method set forth in Example 1 of German patent 1,243,187 yielded 368.4 g of a mixture of indanes and tetralines, consisting of 54.9% of 1,1,3,4,4,6-hexamethyltetraline, 38.9% of 1,1,2,3,3,5-hexamethylindane, 2.2% of 1,1,3,5-tetramethyl-3-(propyl-2)indane and 1.1% of 1,1,2,3,5-pentamethyl-3-ethyl-indane as the main components.

EXAMPLES 2-10

The following mixtures of indanes and tetralines were prepared by cycloalkylation of 629 g of p-cymene:

394.1 g from 143.8 g of 2-methylbutene-2 followed by 172.5 g of 2,3-dimethylbutene-1. Main components: 47.2% of 1,1,3,4,4,6-hexamethyltetraline, 44.0% of 1,1,2,3,3,5-hexamethylindane, 1.8% of 1,1,2,3,5-pentamethyl-3-ethylindane and 1.6% of 1,1,3,5-tetramethyl-3-(propyl-2)indane.

392.1 g from 172.5 g of 2,3-dimethylbutene-1 followed by 143.8 g of 2-methylbutene-2. Main components: 47.0% of 1,1,3,4,4,6-hexamethyltetraline, 44.5% of 1,1,2,3,3,5-hexamethylindane, 1.6% of 1,1,3, 5-tetramethyl-3-(propyl-2)indane and 1.0% of 1,1,2,3,5-pentamethyl-3-ethylindane.

389.0 g from 172.5 g of 3,3-dimethylbutene-1 followed by 143.8 g of 2,methylbutene-2. Main components: 48.8% of 1,1,3,4,4,6-hexamethyltetraline, 45.1% of 1,1,2,3,3,5-hexamethylindane, 1.2% of 1,1,2,3,5-pentamethyl-3-ethylindane, 1.1% of 1,1,3,5-tetramethyl-3-(propyl-2)indane.

385.7 g from 143.8 g of 2-methylbutene-2 mixed with 172.5 g of 3,3-dimethylbutene-1. Main components: 61.3% of 1,1,2,3,3,5-hexamethylindane, 28.6% of 1,1,3,4,4,6-hexamethyltetraline, 2.1% of 1, 1,2,3,5-pentamethyl-3-ethylindane, 1.1% of 1,1,3,5-tetramethyl-3-ethylindane, 0.7% of 1,1,3,6-tetramethyl-3-(propyl-2)indane and 0.6% of 1,1,3,5-tetramethyl-3-(propyl-2)-indane.

383.9 g from 57.5 g of 2-methylbutene-2 followed by 276 g of 2,3-dimethylbutene-1. Main components: 76.4% of 1,1,3,4,4,6hexamethyltetraline, 16.8% of 1,1,2,3,3,5-hexamethylindane, 3.2% of 1,1,3,5-tetramethyl-3-(propy 1-2)indane, 1.0% of 1,1,2,3,5-pentamethyl-3-ethylindane, 0.5% and 0.3% of 1,1,3,6-tetramethyl-3- (propyl-2) -indane.

380.8 g from 57.5 g of 2-methylbutene-2 mixed with 276 g of 2,3-dimethylbutene-1. Main components: 80.6% of 1,1,3,4,4,6-hexamethyltetraline, 13.8% of 1,1,2,3,3,5-hexamethylindane, 3.4% 1,1,3,5-tetramethyl-3- (propyl-2) indane, 0.6% of 1,1,3,5-tetramethyl-3-ethylindane and 0.2% of 1,1,2,3,5-pentamethyl-3-ethylindane.

376.1 g from 170.3 g of 2-methylbutene-2 mixed with 69.0 g of 2,3-dimethylbutene-1. Main components: 76.5% of 1,1,2,3,3,5-hexamethylindane, 24.5% of 1,1,3,4,4,6-hexamethyltetraline, 2.1% of 1,1,2,3,5-pentamethyl-3-ethylindane, 0.9% of 1, 1,3,5-tetramethyl-3-(propyl-2) indane, 0.6% of 1,1,3,5-tetramethyl- 3-ethylindane.

396.7 g from 28.8 g of 2-methylbutene-2 mixed with 310.5 g of 2,3-dimethylbutene-1. Main components: 88.4% of 1,1,3,4,4,6-hexa-methyltetraline, 6.4% of 1,1,2,3,3,5-hexamethylindane, 3.3% of 1, 1,3, 5-tetramethyl-3-(propyl-2)indane, 0.5% of 1,1,3,6-tetramethyl-3-(propyl-2)indane and 0.3% of 1,1,3,5-tetramethyl-3-ethylindane.

EXAMPLE 11-14

The following mixtures of acetylindanes and acetyltetralines were obtained by acetylation of 500 g of mixtures of indanes and tetralines according to the method set forth in Example 7 of European patent 0,071,006:

557.0 g from the mixture of indanes and tetralines of Example 1. Main components: 56.5% of 7-acetyl-1,1,3,4,4,6hexamethyltetraline, 40.6% 6-acetyl-1,1,2,3,3,5-hexamethylindane, 1.6% 6-acetyl-1,1,3,5-tetramethyl-3-(propyl-2) indane and 1.0% 6-acetyl-1,1,2,3,5-pentamethyl-3-ethyl-indane. Melting range 31.8°–33.8° C.

560.4 g from the mixture of indanes and tetralines of Example 7. Main components: 77.5% of 7-acetyl-1,1,3,4,4,6-hexamethyltetraline, 17.7% of 6-acetyl-1,1,2,3,3,5-hexamethylindane, 3.2% of 6-acetyl-1,1,2,3,3,5-tetramethyl-3(propyl-2)indane and 1.0% of 6-acetyl-1,1,2,3,5-pentamethyl-3-ethyl-indane. Melting range of mixture is 36.5°–44.2° C.

538 g from the mixture of indanes and tetralines of Example 8. Main components: 81.3% of 7-acetyl-1,1,3,4,4,6-hexamethyltetraline, 14.3% of 6-acetyl-1,1,2,3,3,5-hexamethylindane, 3.6% of 6-acetyl-1,1,3,5-tetramethyl-3-(propyl-2)indane and 0.2% of 6-acetyl-1,1,2,3,5-pentamethyl-3-ethyl-indane.

556.4 g from the mixture of indanes and tetralines of Example 9. Main components: 69.9% of 6-acetyl-1,1,2,3,3,5-hexamethylindane, 26.4% of 7-acetyl- 1,1,2,4,4,6hexamethyltetraline, 2.1% of 6-acetyl-1,1,3,5-tetramethyl-3-(propyl-2)-indane and 0.9% of 6-acetyl-1,1,2,3,5-pentamethyl-3-ethyl-indane. Melting range of mixture is 45.5°–50.7° C.

EXAMPLE 15

The following mixtures, homogeneous and liquid at room temperature, were prepared:

a. 70% by weight of the mixture of acetylidanes and acetyltetralines of Example 11 and 30% by weight of Floralyn (R) (hydrogenated methyl ester of rosin).

b. 70% by weight of the mixture of acetylidanes and acetyltetralines of Example 14 and 30% by weight of Floralyn (R) (hydrogenated methyl ester of rosin).

c. 70% by weight of the mixture of acetylindanes and acetyltetralines of Example 11, 20% by weight of Floralyn (R) (hydrogenated methyl ester of rosin) and 10% by weight of isopropyl myristinate.

d. 80% by weight of the mixture of acetylindanes and acetyltetralines of Example 11 and 20% by weight of Floralyn (R) (hydrogenated methyl ester of rosin).

e. 80% by weight of the mixture of acetylindanes and acetyltetralines of Example 11, 10% by weight of Floralyn (R) (hydrogenated methyl ester of rosin) and 10% by weight of isopropyl myristinate.

f. 80% by weight of the mixture of acetylindanes and acetyltetralines of Example 11 and 20% by weight of isopropyl myristinate.

g. 70% by weight of the mixture of acetylindanes and acetyltetralines of Example 11 and 15% by weight of Floralyn (R) (hydrogenated methyl ester of rosin) and 15% by weight of isopropyl myristinate.

None of the above mixtures showed solidification or crystallization after repeated freezing at −20° C. for an overnight period and warming up again to room temperature, also not after the addition of seed crystals o both 7-acetyl-1,1,13,4,4,6-hexamethyltetraline and/or 6-acetyl-1,1,2,3,3,5-hexamethylindane.

EXAMPLE 16

Tonalid ® (7-acetyl-1,1,3,4,4,6-hexamethyltetraline) was dissolved at 5% by weight in Floralyn ® (hydrogenated methyl ester of rosin). The concentration of Tonalid was increased by weight and subjected to the freeze test of Example 15. Solidification at room temperature occurred at concentrations of Tonalid above 50% by weight.

EXAMPLE 17

The odor of a solution C from Example 15 was compared with a 70% solution in diethyl phtalate of a mixture of Tonalid ® (7-acetyl-1,1,3,4,4,6-hexamethyltetraline) and Phantolid ® (6-acetyl-1,1,2,3,3,5-hexamethylindane) of comparable ratio, by perfumers skilled in the art. The odor of solution C from Example 15 was described as full, sweet, bright musk with a floral powdery background, being surprisingly sweeter and more floral and having more topnote than the other solution.

EXAMPLE 18

The following perfume formulations were prepared:

| | Parts by Weight |
|---|---|
| A. Methyloctlactone (PFW) | 3 |

-continued

| | Parts by Weight |
|---|---|
| Frutalone (PFW) | 6 |
| Costaulon, 10% in DPG (PFW) | 6 |
| Seamoss (PFW) | 6 |
| Cypronat (Henkel) | 6 |
| Pivarose (Quest) | 8 |
| Rosenitrile (PFW) | 15 |
| Diphenyl Oxide | 15 |
| Elintaal (Quest) | 15 |
| Phenylethyl acetate | 30 |
| Hexylcinnamic aldehyde | 50 |
| Cyclaprop (IFF) | 50 |
| Vertenex Regular (IFF) | 50 |
| Vertofix Coeur (IFF) | 50 |
| Oxysesquine (PFW) | 50 |
| Methylionone Gamma A (IFF) | 50 |
| Lilial (Givaudan) | 60 |
| Tetrahydromuguol (IFF) | 80 |
| Solution C from Example 15 | 200 |
| Orange Isolate (PFW) | 250 |
| Total | 1000 |

B. The formulation A wherein the solution C from Example 15 was replaced by the same amount of a mixture of 43% Tonalid ® (PFW), 27% Phantolid (PFW) and 30% diethyl phtalate.

Wash tests in a regular household washing machine were performed on cotton and cotton/polyester towels with both formulation at 0.4% in liquid detergent. The odor of both the wet and the dried towels after wash was found surprisingly sweeter and fuller in case of formulation A.

What is claimed is:

1. A mixture of acetylpolyalkylindanes and acetylpolyalkyltetralines prepared by cycloalkylation of p-cymene and/or p,α-dimethylstyrene and/or 8-p-cymenyl halides and/or 8-p-cymenyl alcohol with a mixture of alkenes of one ore more methylbutene Isomers and one or more dimethylbutene isomers in a ratio of 0.09–2.5 by weight, in the presence of a Lewis acid and in substantial absence of elemental Iodine, followed by acetylation of the intermediate mixture of polyalkylindanes and polyalkyltetralines.

2. The mixture of acetylindanes and acetyltetralines according to claim 1 containing at least 20% by weight of 6-acetyl-1,1,2,3,3,5-hexamethylindane.

3. The mixture of acetylindanes and acetyltetralines according to claim 1 containing at least 20% by weight of 7-acetyl-1,1,3,4,4,6-hexamethyltetraline.

4. The mixture of acetylindanes and acetyltetralines according to claim 1 further comprising between 10% and 75% by weight of the methyl ester of rosin.

5. The mixture of acetylindanes and acetyltetralines according to claim 1 further comprising between 10% and 75% by weight of hydrogenated methyl ester of rosin.

6. The mixture of acetylindanes and acetyltetralines according to claim 1 further comprising between 10% and 75% by weight of hydrogenated methyl ester of rosin and between 5–80% by weight of isopropyl myristate.

7. A mixture according to claim 1 prepared from p-cymene and/or p,α-dimethylstyrene and/or 8-p-cymenyl halides and/or 8-p-cymenyl alcohol and a combination of alkenes of one or more methylbutenes selected from the group of 2-methylbutene-2 and 2-methylbutane-1 and one or more dimethylbutenes selected from the group 3,3-dimethylbutene-1,2,3-dimethylbutene-1 and 2,3-dimethylbutene-2.

8. The mixture of indanes and tetralines according to claim 7 containing at least 20% by weight of 1,1,3,3,5-hexamethylindane.

9. The mixture of indanes and tetralines according to claim 7 containing at least 20% by weight of 1,1,3,4,4,6-hexamethyltetraline.

10. The mixture of acetylindanes and acetyltetralines prepared by acetylation of the mixture of indanes and tetralines of claim 7.

11. A process for enhancing the aroma of a perfume composition or perfumed article comprising the step of admixing the perfume composition or perfumed article with an olfactorily active amount of a mixture according to claim 1.

12. Process for the preparation of an odorant, comprising cycloalkylating p-cymene and/or p,α-dimethylstyrene and/or 8-p-cymenyl halides and/or 8-p-cymenyl alcohol with a mixture of alkenes of one or more methylbutane Isomers and one or more dimethylbutene isomers in a ratio of 0.09–2.5 by weight, in the presence of a Lewis acid and in substantial absence of elemental iodine, followed by acetylation of the intermediate mixture of polyalkylindanes and polyalkyltetralines.

13. A process for using the mixture of claim 1 as an odorant in soap and detergent compositions comprising adding an olfactorily active amount of said mixture to the soap or detergent composition while it is being formulated to impart the desired aroma to said soap or detergent.

* * * * *